(12) United States Patent
Ding et al.

(10) Patent No.: US 7,005,555 B2
(45) Date of Patent: Feb. 28, 2006

(54) PROCESS FOR SEPARATING AND RECYCLING OXYGENATE(S) TO AN OXYGENATE-TO-OLEFIN REACTOR

(75) Inventors: Zhong Yi Ding, Houston, TX (US); James Richardson Lattner, Seabrook, TX (US); Paul N. Chisholm, Houston, TX (US); Jeffrey Alan Kabin, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 392 days.

(21) Appl. No.: 10/603,846

(22) Filed: Jun. 25, 2003

(65) Prior Publication Data

US 2004/0267069 A1   Dec. 30, 2004

(51) Int. Cl.
   *C07C 1/20*   (2006.01)
(52) U.S. Cl. .................. 585/638; 585/639; 585/640
(58) Field of Classification Search ............... 585/638, 585/639, 640
   See application file for complete search history.

(56) References Cited

U.S. PATENT DOCUMENTS

| | | | |
|---|---|---|---|
| 3,554,895 A | 1/1971 | McRae et al. | 204/301 |
| 4,174,370 A | 11/1979 | Oude Alink et al. | 422/12 |
| 4,957,640 A | 9/1990 | Treybig et al. | 252/8.555 |
| 5,000,873 A | 3/1991 | Fisk et al. | 252/391 |
| 5,194,143 A | 3/1993 | Roling | 208/291 |
| 5,264,114 A | 11/1993 | Dunbar | 208/48 HA |
| 5,939,362 A | 8/1999 | Johnson et al. | 507/939 |
| 6,121,504 A | 9/2000 | Kuechler et al. | 585/640 |
| 6,235,961 B1 | 5/2001 | Kurukchi | 585/854 |
| 6,254,779 B1 | 7/2001 | Jeffery et al. | 210/620 |
| 6,403,854 B1 | 6/2002 | Miller et al. | 585/638 |
| 6,432,355 B1 | 8/2002 | Bakeev et al. | 422/9 |
| 6,459,009 B1 | 10/2002 | Miller et al. | 585/809 |
| 6,482,998 B1 | 11/2002 | Kuechler et al. | 585/638 |
| 2002/0020293 A1 | 2/2002 | De Poitiers et al. | 95/149 |
| 2003/0004386 A1 | 1/2003 | Lattner et al. | 585/804 |

FOREIGN PATENT DOCUMENTS

| | | |
|---|---|---|
| DE | 2 241 476 | 3/1974 |
| GB | 1 330 604 | 9/1973 |

OTHER PUBLICATIONS

Raab, M. "*Caustic Scrubbers can be Designed for Exacting Needs,*" Oil & Gas Journal, vol. 74, No. 41, pp. 120-125, (1976).

*Primary Examiner*—Thuan D Dang (57) ABSTRACT

The present invention is a process for producing olefin(s) from oxygenate(s). The process removes oxygenate(s) including carbon dioxide in the bottoms of the quench stream and recycles the oxygenate(s) back to the reactor. Carbon dioxide is removed from the quench bottoms before returning oxygenate(s) in the quench bottoms stream to the reactor.

14 Claims, 2 Drawing Sheets

PROCESS FOR SEPARATING AND RECYCLING OXYGENATE(S) TO AN OXYGENATE-TO-OLEFIN REACTOR

FIELD OF THE INVENTION

The present invention relates to a process for recovering unreacted oxygenate(s) leaving an oxygenate-to-olefin reactor.

BACKGROUND OF THE INVENTION

Olefin(s) are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenate(s), especially alcohols, are convertible into light olefin(s). This process is referred to as the oxygenate-to-olefin process. Typically, the preferred oxygenate for light olefin production is methanol. The process of converting methanol-to-olefin(s) is called the methanol-to-olefin(s) process.

There are numerous technologies available for producing oxygenate(s), and particularly methanol, including fermentation or reaction of synthesis gas derived from natural gas, petroleum liquids, carbonaceous materials including coal, recycled plastics, municipal waste or any other organic material. The most common process for producing methanol is a two-step process of converting natural gas to synthesis gas. Then, synthesis gas is converted to methanol.

Generally, the production of synthesis gas involves a combustion reaction of natural gas, mostly methane, and an oxygen source into hydrogen, carbon monoxide and/or carbon dioxide. Synthesis gas production processes are well known, and include conventional steam reforming, autothermal reforming or a combination thereof.

Synthesis gas is then processed into methanol. Specifically, the components of synthesis gas (i.e., hydrogen, carbon monoxide and/or carbon dioxide) are catalytically reacted in a methanol reactor in the presence of a heterogeneous catalyst. For example, in one process, methanol is produced using a copper/zinc oxide catalyst in a water-cooled tubular methanol reactor.

The methanol is then converted to olefin(s) in a methanol-to-olefin(s) process. The methanol-to-olefin(s) reaction is highly exothermic and has a large amount of water. Water comprises as much as one half of the total weight of the output stream of the reactor or effluent stream. Consequently, the water must be removed by condensation in a quench device to isolate the olefin product. A quench device cools the effluent stream to the condensation temperature of water.

The effluent stream of an oxygenate-to-olefin reactor also contains byproducts including oxygenate byproducts such as organic acids, aldehydes and/or ketones. Carbon dioxide is also a byproduct of the oxygenate to olefin reaction. Furthermore, depending upon operating conditions, unreacted methanol is likely to be present in the effluent of the oxygenate-to-olefin reaction.

U.S. Pat. Nos. 6,482,998 and 6,121,504 describe an oxygenate-to-olefin process that includes a quench tower for removal of water produced in the oxygenate-to-olefin reactor. Unreacted oxygenate feed (typically methanol) that is liquid under quenching conditions is removed from the quench tower as a heavy product fraction. The unreacted oxygenate feed is separated from water in the quench medium in a fractionation tower.

U.S. Pat. No. 6,403,854 describes a two stage solids wash and quench for use with the oxygenate conversion process where catalyst fines are removed from the effluent stream through a first quench stage. The bottoms of the quench include water, alcohols, ketones and neutralized organic acids that have a boiling point greater than water. The quench medium is a portion of the quench bottoms that is mixed with a neutralization stream and purified water stream. Therefore acids such as formic acid, acetic acid, butyric acid and propanoic acid can be neutralized. The neutralization material can be caustic, amines or ammonia.

Notwithstanding the improvements in technology relating to the removal of impurities from the effluent stream of an oxygenate-to-olefin reactor with a quench device, it would be desirable to have a process for quenching an oxygenate-to-olefin effluent stream that will remove carbon dioxide as well as organic acids, aldehydes and/or ketones in the quench bottoms stream. The present invention addresses these and other needs.

Notwithstanding the recent improvements in the state of the art, there is still a need for a process that efficiently recovers and uses oxygenate(s) in the effluent stream of an oxygenate-to-olefin reactor. The present invention satisfies these and other needs.

SUMMARY OF THE INVENTION

The present invention is a process for producing olefin(s) from oxygenate(s) that has greater efficiency from its beneficial integration than previously disclosed in the prior art. The process removes oxygenate(s) including carbon dioxide in the bottoms of the quench stream and recycles the oxygenate(s) back to the reactor. Carbon dioxide is removed from the quench bottoms before returning oxygenate(s) in the quench bottoms stream to the reactor. Particularly, the present invention comprises contacting an oxygenate feed stream with an oxygenate-to-olefin catalyst to produce an effluent stream comprising carbon dioxide, oxygenate(s), water and olefin(s).

The effluent stream is then quenched to produce a quenched effluent stream comprising olefin(s) and quench bottoms stream. The carbon dioxide is removed from the quench bottoms stream. Then, a majority of the oxygenate(s) are separated from water in the quench bottoms stream and are combined with the oxygenate feed stream.

According to another embodiment of the present invention there is a process for making polyolefin(s) from an oxygenate feed stream. The process comprises contacting an oxygenate feed stream with an oxygenate-to-olefin catalyst to produce an effluent stream comprising oxygenate(s), carbon dioxide, water and olefin(s). The effluent stream is quenched to produce an olefin stream, and a quench bottoms stream comprising carbon dioxide, oxygenate(s) and water. Carbon dioxide is removed from the quench bottoms stream. A majority of the oxygenate(s) are separated from a majority of the water in the quench bottoms stream. A majority of the oxygenate(s) are combined with the oxygenate feed stream. Finally, olefin(s) in the olefin stream are converted to polyolefin(s).

There is another embodiment according to any process disclosed herein wherein the step of removing carbon dioxide from the quench bottoms stream comprises lowering the pH of the quench bottoms stream.

There is another embodiment according to any process disclosed herein wherein the step of lowering the pH includes combining an acidic composition with the quench bottoms stream, preferably an inorganic acid, more preferably an inorganic acid selected from the group consisting of hydrochloric acid, nitric acid, sulfuric acid and mixtures thereof.

There is another embodiment according to any process disclosed herein wherein the acidic composition is an organic acid, preferably formic acid, acetic acid, propanoic acid, butyric acid, more preferably acetic acid.

There is another embodiment according to any process disclosed herein wherein the quench bottoms stream is separated into a hydrocarbon phase and an aqueous phase. As used herein, the term hydrocarbon phase includes hydrophobic phase that is immiscible in water under a particular set of conditions. It includes aliphatic hydrocarbons. The aqueous phase includes the components that are miscible in water under particular conditions. Th aqueous phase is then processed according to the previously described step of separating carbon dioxide.

There is another embodiment according to any process disclosed herein wherein the hydrocarbon phase comprises aromatic hydrocarbons.

There is another embodiment according to any process disclosed herein wherein the hydrocarbon phase comprises products of aldol condensation of aldehydes and/or ketones.

There is another embodiment according to any process disclosed herein wherein the aqueous phase comprises organic acids, typically in their salt form.

There is another embodiment according to any process disclosed herein wherein the aqueous phase comprises alcohol.

There is another embodiment according to any process disclosed herein wherein the aqueous phase contains catalyst fines.

There is another embodiment according to any process disclosed herein wherein the step of separating carbon dioxide from the quench bottoms stream removes more than 10 wt. %, preferably from about 50 wt. % to about 99 wt. %, more preferably from about 80 wt. % to about 95 wt. %, most preferably about 90 wt. % of the carbon dioxide in the quench bottoms stream.

There is another embodiment according to any process disclosed herein wherein the quench medium comprises the aqueous phase of the quench bottoms stream.

There is another embodiment according to any process disclosed herein wherein the quench medium has a pH ranging from 7.1 to about 11.5, preferably from 7.5 to about 11.0, more preferably from 8.0 to about 10.0, and most preferably of about 9.

There is another embodiment according to any process disclosed herein wherein the step of separating carbon dioxide from the quench bottoms stream occurs at a pH ranging from about 6 to about 9 more preferably from about 6.5 to about 8.5, most preferably of about 7.

According to one embodiment of the present invention there is an apparatus for producing olefin(s) from an oxygenate feed stream. The apparatus comprises:

(a) a reactor having a reactor inlet and a reactor outlet;

(b) a quench device having a quench inlet in fluid communication with the reactor outlet, a quench overhead outlet and a quench bottoms outlet;

(c) a first conduit having a downstream end and an upstream end, the upstream end being in fluid communication with the quench bottoms outlet;

(d) a separation vessel having a first vessel inlet in fluid communication with the downstream end, a first vessel outlet and a second vessel outlet, wherein the separation vessel is configured to separate a gaseous component of a liquid mixture from the liquid mixture and remove the gaseous component through the first vessel outlet and a liquid component through the second vessel outlet;

(e) a distillation column having a column inlet, an overhead column outlet and a bottoms column outlet, wherein the column inlet is in fluid communication with the second vessel outlet and the overhead column outlet is in fluid communication with the reactor inlet; and (f) an acid inlet configured to introduce an acid component in the first conduit and/or the separation vessel.

DETAILED DESCRIPTION OF THE INVENTION

Introduction and Overview

The present invention is a process for making an olefin stream from an oxygenate feed stream. The oxygenates are converted into olefin(s) in a reactor to produce an effluent stream that in addition to the olefin(s), also has carbon dioxide as a byproduct. At least a portion of the carbon dioxide is removed from the effluent stream in a quenching step and more carbon dioxide is removed from the effluent stream in an alkaline wash step. Additionally, corrosion of the quench device and other downstream equipment is inhibited under at least one embodiment of the present invention.

Figure 1:
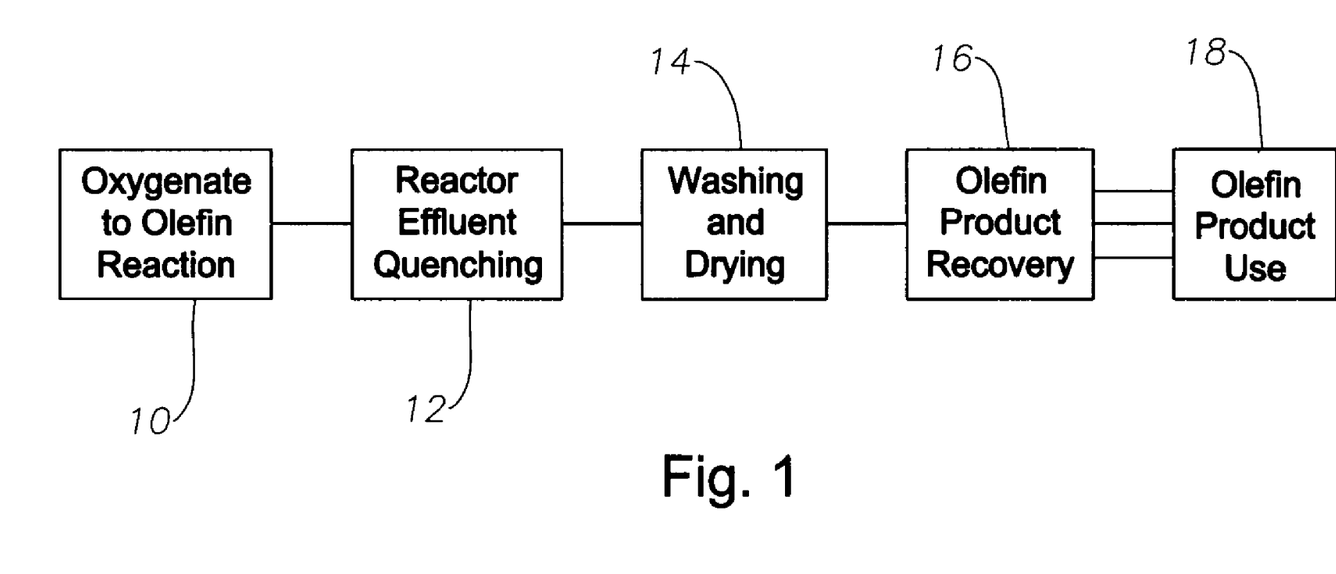
FIG. 1 illustrates the overall process of an oxygenate-to-olefin plant according to one embodiment of the present invention.

To aid in the understanding of the present invention, a brief overview of the processing steps of producing and using one or more olefin(s) from an oxygenate feed stream, according to one embodiment, is discussed with reference to FIG. 1. The oxygenate-to-olefin reaction 10 converts an oxygenate feed stream into olefin(s). The gaseous output stream of an oxygenate-to-olefin reaction is defined as the effluent stream. The reactor effluent stream is particularly the gaseous output stream from the point the effluent stream exits a reactor to the point the gaseous output stream is quenched.

The step of quenching 12 cools the reactor effluent stream to separate water from the effluent stream and to produce a quenched effluent stream. According to one embodiment, carbon dioxide is separated in a quench device from the effluent stream, in another embodiment, alcohol, aldehydes and/or ketones are separated from the effluent stream in the quench device. These alcohols, aldehydes and ketones can be recycled in an oxygenate recycle stream back to the oxygenate feed stream. Optionally, carbon dioxide is purged from this oxygenate recycle stream. Optional compression of the quenched effluent stream is included in the step of quenching 12. A quenched effluent stream is an effluent stream after at least one stage of quenching.

The quenched effluent stream then undergoes a collective step of washing and drying 14 to produce a dried effluent stream. Washing the quenched effluent stream separates acidic components, such as carbon dioxide, with an alkaline wash. The alkaline wash produces a used alkaline wash medium. In one embodiment, the used alkaline wash medium is combined with the quench medium to adjust the pH of the quench device. Aldehydes and/or ketones can be removed according to one operation scheme of the alkaline wash. In another embodiment, additional water washing and or washing with other extractants can remove oxygenate(s) in the effluent stream.

Drying follows washing and removes water that is saturated in the quenched effluent stream. Optionally, the washing and drying stage 14 includes other processing steps to remove additional oxygenates.

The dried effluent stream then undergoes a step of recovering the olefin(s) in one or more olefin product(s) 16. Particularly, light olefin(s), i.e. ethylene and propylene, are recovered in an acceptable grade of purity for a particular application. Thereafter, the recovered olefin product(s) are used in various product applications 18, for example in a polymerization process to make polyolefin product(s). The present invention is an improvement to the process of making olefin(s) from an oxygenate feed stream. Accordingly, the present invention including a more detailed discussion of each step in the manufacture and use of olefin(s) from an oxygenate feed stream is discussed below.

The Oxygenate-to-Olefin Reaction

Figure 2:
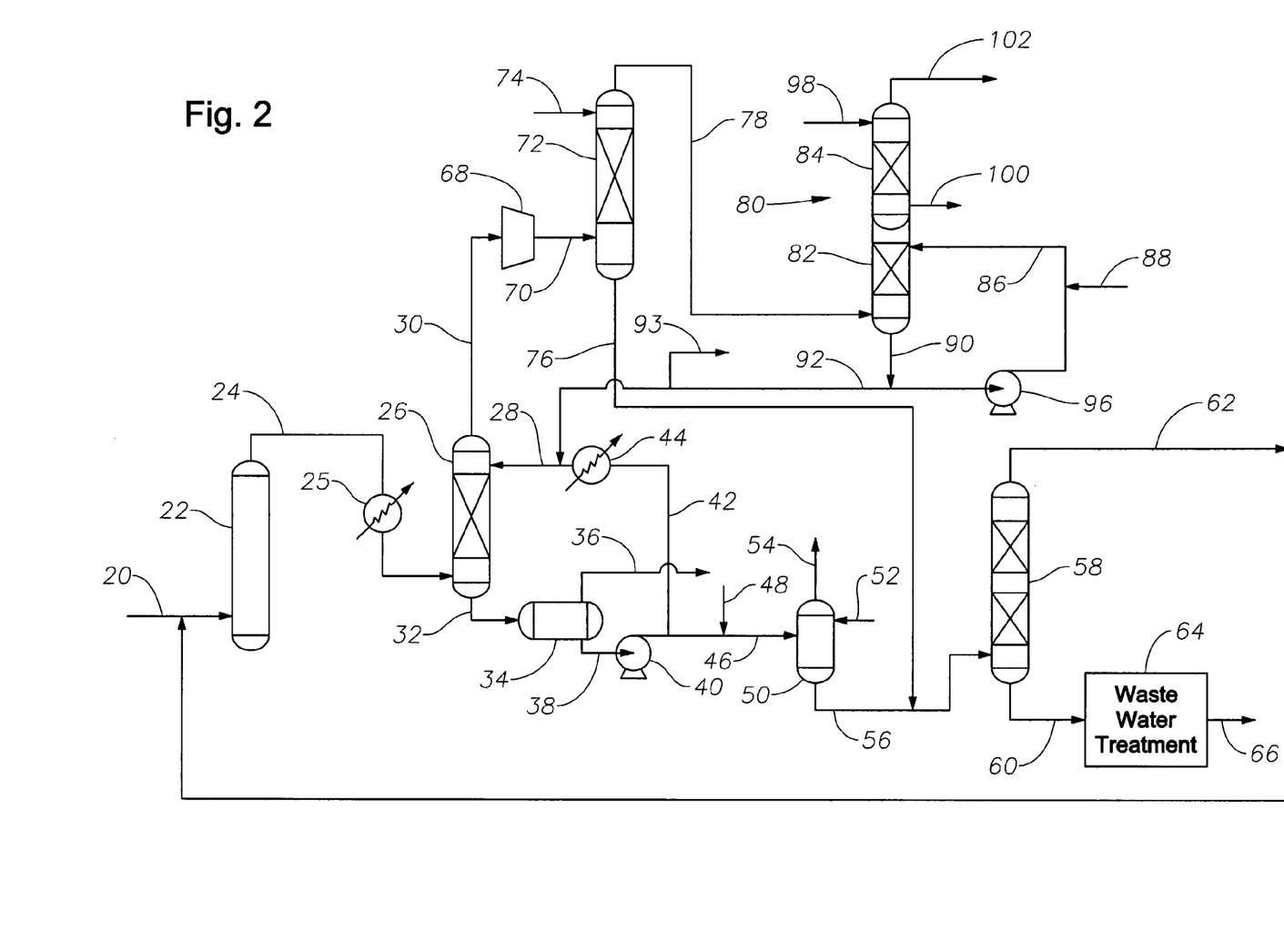
FIG. 2 illustrates a process for purifying the effluent stream of the oxygenate-to-olefin reactor.

As shown in FIG. 2, an oxygenate feed stream is fed along line 20 into an oxygenate-to-olefin reactor 22 producing a reactor effluent stream that is withdrawn along line 24. The reactor 22 uses a catalyst, for example, a molecular sieve catalyst that comprises a molecular sieve catalyst composition.

As noted, oxygenate-to-olefin processes typically use molecular sieve catalysts or molecular sieve catalyst compositions. The molecular sieve catalyst compositions have molecular sieve and binder and/or matrix material. The molecular sieve catalysts are prepared according to techniques that are known to a person of ordinary skill in the art.

Molecular sieves are disclosed in PCT Publication Nos. WO 03/000412 and WO 03/000413, the contents of which are incorporated herein by reference. Preferably, the molecular sieve is a zeolitic or zeolitic-type molecular sieve. Alternatively, the preferred molecular sieve is an aluminophosphate (ALPO) molecular sieves and/or silicoaluminophosphate (SAPO) molecular sieves and substituted, preferably metal substituted, ALPO and/or SAPO molecular sieves including the molecular sieves that are intergrowth materials having two or more distinct phases of crystalline-structures within one molecular sieve composition.

Binder materials that are useful alone or in combination include various types of hydrated alumina, silicas, and/or other inorganic oxide sol. In one embodiment, the binders are alumina sols including Nalco 8676 available from Nalco Chemical Co., Naperville, Ill. and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example, silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

Molecular sieve catalysts are useful for conversion of a feed stream that contains one or more aliphatic-containing compounds. The one or more aliphatic-containing compounds are disclosed in PCT Publication Nos. WO 03/000412 and WO 03/000413, the contents of which are incorporated herein by reference.

In a preferred embodiment of the process of the invention, the aliphatic feed stream is an oxygenate feed stream. Particularly, an oxygenate feed stream is a feed stream that comprises one or more organic compound(s) containing at least one oxygen atom. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the oxygenate feed stream comprises oxygenates selected from one or more of methanol, ethanol, dimethyl ether, diethyl ether or a combination thereof, more preferably methanol and dimethyl ether, and most preferably methanol.

In one embodiment, the oxygenate feed stream is produced from an integrated process for producing oxygenates, particularly alcohols, from a hydrocarbon feedstock, preferably a hydrocarbon gas feedstock, more preferably methane and/or ethane. A method of preparing an alcohol feedstock is disclosed in PCT Publication Nos. WO 03/000412 and WO 03/000413, the contents of which are incorporated herein by reference. The methanol production process produces an oxygenate containing stream, or crude methanol, typically contains the alcohol product (including methanol, ethanol and fusel oil) and various other components such as ethers, particularly dimethyl ether, ketones, aldehydes, as well as dissolved gases such as hydrogen methane, carbon dioxide and nitrogen. The oxygenate containing stream, crude methanol, in the preferred embodiment is passed through a well known purification processes, distillation, separation and fractionation, resulting in a purified oxygenate containing stream, for example, commercial Grade A and AA methanol. This purified oxygenate containing stream is used in one embodiment as the oxygenate feed stream. Non-limiting examples of a process for producing an oxygenate feed stream from hydrocarbons and using it to produce olefin(s) is described in EP-B-0 933 345, which is herein fully incorporated by reference.

The aliphatic feed stream, preferably oxygenate feed stream, discussed above is converted primarily into one or more olefin(s). The olefin(s) or olefin monomer(s) produced from the aliphatic feed stream typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefin(s) having 4 to 18 carbon atoms, conjugated or non-conjugated dienes, polyenes, vinyl monomers and cyclic olefin(s). PCT Publication Nos. WO 03/000412 and WO 03/000413 for a more complete description of the olefin(s) produced, the content of these publications are incorporated herein by reference. Most preferably, the olefin(s) produced are ethylene, propylene or butene often referred to as prime olefin(s) or light olefin(s).

In one embodiment of the process for conversion of an oxygenate feed stream, the total amount of olefin(s) produced based on the total weight of hydrocarbon produced is greater than 50 weight percent, preferably greater than 60 weight percent, more preferably greater than 70 weight percent, and most preferably greater than 75 weight percent.

The aliphatic feed stream, preferably an oxygenate feed stream, in one embodiment, contains one or more diluents, typically used to reduce the concentration of the active ingredients in the oxygenate feed stream, and are generally non-reactive to the active ingredients in the oxygenate feed stream or molecular sieve catalyst composition. Non-limiting examples of diluents are disclosed in PCT Publication Nos. WO 03/000412 and WO 03/000413, the contents of which are incorporated herein by reference. The most preferred diluents are water and nitrogen, with water being particularly preferred.

In one embodiment, other hydrocarbons are added to the aliphatic feed stream, preferably oxygenate feed stream, either directly or indirectly, and include olefin(s), paraffin(s), aromatic(s) (see for example, U.S. Pat. No. 4,677,242, addition of aromatics) or mixtures thereof, preferably propylene, butene, pentene, and other hydrocarbons having 4 or more carbon atoms, or mixtures thereof.

The process for converting an aliphatic feed stream, especially an oxygenate feed stream in the presence of a molecular sieve catalyst composition is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred oxygenate-to-olefin reactor is a riser reactor. Riser reactors are generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one embodiment, the reactor effluent stream comprises ethylene and propylene, C4+olefin(s), methane, C2+parrafins, water, unreacted oxygenate(s), and oxygenate hydrocarbons. In another embodiment, the reactor effluent stream comprises from about 30 wt. % to about 70 wt. % water, preferably, from about 35 wt. % to about 70 wt. % water; more preferably from about 40 wt. % to about 65 wt. % water expressed as a percentage of the total weight of the reactor effluent stream.

In the embodiment illustrated in FIG. 2, the reactor effluent stream exits the reactor 22 through particle size separators and travel along line 24. The reactor effluent stream contains catalyst fines. According to one embodiment, the reactor effluent stream has about 2 wt. % or less, preferably about 1 wt. % or less, more preferably from about 0.005 wt. % to about 0.5 wt. % catalyst fines based upon the total weight of the reactor effluent stream;

In still another embodiment, there is a process for quenching an effluent stream, and particularly a reactor effluent stream, from an oxygenate-to-olefin reactor that comprises providing a reactor effluent stream that contains 40 wt. % or more water, from about 50 wppm to about 2000 wppm carbon dioxide and from about 40 wt. % to about 60 wt. % olefin(s) based upon the composition of the reactor effluent stream. There is an embodiment according to any process disclosed herein wherein the reactor effluent stream further comprises from about 0.05 wt. % to about 5 wt. %, preferably from about 0.1 wt. % to about 3 wt. %, more preferably from about 0.2 wt. % to about 3 wt. %, even more preferably from about 1 wt. % to about 2 wt. %, most preferably of about 1.5 wt. % alcohol based upon the total weight of the reactor effluent stream.

There is another embodiment according to any process disclosed herein wherein the reactor effluent stream further comprises from about 0.05 wt. % to about 5 wt. %, preferably from about 0.1 wt. % to about 3 wt. %, more preferably from about 0.2 wt. % to about 3 wt. %, even more preferably from about 1 wt. % to about 2 wt. %, most preferably of about 1.5 wt. % methanol based upon the total weight of the reactor effluent stream.

The reactor effluent stream is transported along line 24 to a quench device 26, as described below. According to one embodiment, the reactor effluent stream has a dewpoint. By dewpoint it is meant the temperature that a gaseous stream first condenses. The reactor effluent stream remains at a temperature above the dewpoint while it is transported from the reactor effluent stream to the quench device in a first conduit along line 24.

In one embodiment illustrated in FIG. 2, the first conduit is in fluid communication with a heat exchanger system 25. According to one embodiment, the heat exchanger system 25 comprises one or more heat exchanger services, preferably two to four heat exchanger services, most preferably two or three heat exchanger services. Optionally, the heat exchanger system 25 cools the effluent stream, including the reactor effluent stream, to produce a cooled effluent stream. The cooled effluent stream is an effluent stream after at least one stage of cooling before at least one stage of quenching.

Quench, Compression, and Oxygenate Recycle

Following optional cooling, the effluent stream, of one embodiment, travels along line 24 to a quench device 26. The effluent stream (including the reactor effluent stream or the cooled effluent stream) is quenched with a quench medium in the quench device 26 to produce a quenched effluent stream. As used herein, "quench device" is a device for removing a portion of the effluent stream (including the reactor effluent stream or the cooled effluent stream) by establishing a sufficient quantity of liquid quench medium in contact with a gaseous reactor effluent stream which condenses at least a portion of the material in the reactor effluent stream. One example of a quench device in an oxygenateto-olefin product stream is found in U.S. Pat. No. 6,121,504 (direct product quench) fully incorporated herein by reference. A "quench medium" is defined as a liquid that contacts the effluent stream in a quench device.

The quench device in one embodiment has single or multiple stages. The multiple stages of a particular embodiment has preferably two to four stages, more preferably two to three stages. The quench device is optionally in single or multiple housings or towers.

The quench device typically includes internal elements in a contact zone to facilitate intimate contacting of the quench medium with the reactor effluent stream or portions thereof. Contact zone is defined as the zone of the quench device where the effluent stream comes in contact with the quench medium. Internal elements include liquid distributors and contacting devices such as baffles, trays, random packing or structured packing.

Generally, the step of quenching the effluent stream forms a quenched effluent stream and a liquid fraction or quench bottoms stream. As used herein, the terms, "liquid fraction" and "quench bottoms stream" are used interchangeably and refer to the portion of the effluent stream and quench medium that is liquid under quench conditions and includes all streams that contain the condensed portion of the effluent stream and fractions of the condensed effluent stream. The term "quenched effluent stream refers to the portion of the effluent stream that is gaseous after at least one step of quenching.

The quenched effluent stream or "olefin stream" is predominantly gaseous and, in one embodiment, leaves the quench device 26 along line 30. The liquid fraction contains a majority of the catalyst fines in the effluent stream. The liquid fraction is withdrawn along line 32 for additional processing. In one embodiment, a quench medium is supplied to the quench device 26 along line 28. According to one embodiment, the quench medium is an aqueous quench medium. In another embodiment, the quench medium is an aqueous quench medium that is pH adjusted by adding alkaline, preferably caustic. In still another embodiment, the pH is adjusted by adding ammonium or amines.

According to an embodiment, the pH of the quench medium as it enters the quench device 26 is greater than 7. Preferably, the pH of the quench medium as it enters the quench device ranges from about 7.1 to about 11.5, more preferably ranging from about 7.5 to about 11, even more preferably ranging from about 8 to about 10 at the time the quench medium enters the quench device. Most preferably, the pH of the quench medium as it enters the quench device 26 is about 9 at the time the quench medium enters the quench device.

The quench device bottoms temperature is from about 180° F. (82° C.) to about 300° F. (149° C.); preferably from about 180° F. (82° C.) to about 250° F. (121° C.); more preferably about 200° F. (93° C.). The temperature of the quench medium is from about 60° F. (15° C.) to about 200° F. (93° C.); preferably from about 80° F. (27° C.) to about 140° F. (60° C.); more preferably about 110° F. (43° C.). The quench device is operated at a pressure that is from about 15 psig (103 kpag) to about 50 psig (345 kPag); preferably from about 15 psig (103 kPag) to about 40 psig (276 kPag); and more preferably about 20 psig (138 kPag).

The step of contacting the effluent stream with a quench medium removes water from the effluent stream. In one embodiment, the step of contacting the effluent stream with a quench medium removes 95 wt. % or more of the water, preferably 98 wt. % or more, more preferably 99 wt. % or more from the effluent stream based upon the total amount of water in the effluent stream before the effluent stream is quenched.

In one embodiment, a majority of the catalyst fines in the effluent stream is removed in the liquid fraction of the quench device 26. The term "majority" means more than 50%. According to one embodiment, the weight of the catalyst fines in the liquid fraction is about 5 wt. % or less, preferably about 2 wt. % or less, more preferably about 0.1 wt. % or less based on the total weight of the liquid fraction. According to one embodiment, the weight of catalyst fines in the liquid fraction is about 10 wppm or greater based upon the total weight of the liquid fraction.

There is another embodiment according to any process disclosed herein wherein the step of contacting the effluent stream with a quench medium removes 5 wt. % or more, preferably 50 wt. % or more, more preferably 75 wt. % or more, most preferably about 80 wt. % of the carbon dioxide from the effluent stream based upon the total amount of carbon dioxide in the effluent stream before the effluent stream is quenched.

A portion of aldehydes and/or ketones, in one embodiment, are present in the quench bottoms stream. According to one embodiment, the step of contacting the effluent stream with a quench medium removes from about 25 wt. % to about 95 wt. %, preferably from about 40 wt. % to about 90 wt. %, more preferably from about 50 wt. % to about 85 wt. %, of the aldehydes and/or ketones from the effluent stream based upon the total amount of aldehydes and/or ketones in the effluent stream before the effluent stream is quenched.

At a pH of 7 or above, organic acids are also neutralized. By organic acids, it is meant acids that contain one or more carbon atoms that have at least one C—H bond. Such acids include formic acid, acetic acid, propanoic acid and butyric acid. Unless otherwise specifically mentioned the term organic acid, as well as specific organic acids include the salt form. In the neutral salt form, the organic acids are more soluble in water and are more likely to be extracted in the bottoms stream of the quench device. According to one embodiment, the step of contacting the effluent stream with a quench medium or removes 95 wt. % or more, preferably 98 wt. % or more, more preferably 99 wt. % or more of organic acids from the effluent stream based upon the total amount of organic acids in the effluent stream before the effluent stream is quenched.

Oxygenates, including but not limited to unreacted oxygenate feed, particularly alcohol feed and more particularly methanol feed is found in the reactor effluent stream—typically when oxygenate conversion in the oxygenate-to-olefin reactor is less than 100%. Oxygenates, including but not limited to unreacted oxygenates are removed from the effluent stream. In one embodiment, the effluent stream further comprises alcohol. The step of contacting the effluent stream with a quench medium removes 95 wt. % or more, preferably 98 wt. % or more, more preferably 99 wt. % or more of alcohol from the effluent stream based upon the total amount of alcohol in the effluent stream before the effluent stream is quenched.

The quenched effluent stream or portion of the effluent stream that is gaseous after at least one step of quenching, typically comprises light olefin(s) including ethylene, propylene and butylene, dimethyl ether, methane, carbon monoxide, ethane, propane, and any water and unreacted oxygenate(s) such as alcohol (including methanol) that are not condensed during the operation of the quench device. According to some embodiments of the present invention, not all carbon dioxide is removed from the reactor effluent stream by the step contacting the effluent stream with a quench medium. Accordingly, carbon dioxide is found in the quenched effluent stream according to one embodiment of the present invention.

The quench bottoms stream or liquid fraction, of one embodiment, is transported along line 32 to a separation drum 34 where a phase separation occurs between a hydrocarbon phase and an aqueous phase. The hydrocarbon phase optionally comprises one or more of the following: red oil (if any) produced from the aldol condensation of aldehydes and ketones, and any aromatic compounds including alkylated aromatics. The aqueous phase comprises water, oxygenates such as methanol and dissolved carbon dioxide and its respective acid and salt forms and other organic acids such as formic acid, acetic acid, propanoic acid and butyric acid in their respective salt forms. According to one embodiment, the aqueous phase is most likely to contain a majority of the catalyst fines in the quench bottoms stream.

The aqueous phase of the quench bottoms stream is transported from the separation drum 34 along line 38. The aqueous phase of the quench bottoms stream is pumped in a pump 40. At least a portion of the aqueous phase of the quench bottoms stream is transported along line 42 to a heat exchanger 44. The heat exchanger 44 cools the aqueous phase of the quench bottoms stream that is in line 42 thus producing a cooled quench medium that is recycled back to the quench device 26 along line 28. If desired, alkaline is added to the quench medium in line 28 to adjust the pH of the quench medium according to one embodiment. Alternatively, the alkaline can be added in any part of the quench system including but not limited to the quench device, the quench bottoms stream, or along line 42. The quench medium is then introduced into the quench device as set forth above. (Optionally, the source of the quench medium is the quench bottoms stream before the separation drum 34.)

The quench bottoms (in one embodiment the aqueous phase of the quench bottoms stream) is typically transported along line 46. According to one embodiment the quench bottoms stream contains carbon dioxide in the form of dissolved carbon dioxide, carbonic acid, sodium bicarbonate, and sodium carbonate. It is typically desirable to remove carbon dioxide from the quench bottoms stream. In an embodiment, there is a step of separating carbon dioxide from the quench bottoms stream by lowering the pH of the quench bottoms stream. Accordingly, an acidic composition is added along line 48 to the quench bottoms stream, typically represented by line 46. In one embodiment, the acidic composition is an inorganic acid, more preferably hydrochloric acid, nitric acid or sulfuric acid. In another embodiment, the acidic composition is an organic acid preferably acetic acid.

The acid-treated quench bottoms stream is typically moved along line 46 into a separation vessel 50. Alternatively or optionally, the acidic composition can be added directly to the separation vessel 50 along line 52.

There is another embodiment according to any process disclosed herein wherein the step of separating carbon dioxide from the quench bottoms stream occurs at a pH that is from about 6 to about 9 more preferably from about 6.5 to about 8.5, most preferably about 7.

The separation vessel 50 removes carbon dioxide gas through line 54. The carbon dioxide is disposed or otherwise used. In one embodiment, the step of separating carbon dioxide from the quench bottoms stream removes more than 10 wt. %, preferably from about 50 wt. % to about 99 wt. %, more preferably from about 80 wt. % to about 95 wt. %, most preferably about 90 wt. % of the carbon dioxide in the quench bottoms stream.

The degasified quench bottoms stream is defined as the quench bottoms stream after carbon dioxide is removed. It is withdrawn from the separation vessel 50 along line 56. In one embodiment, the quench bottoms stream (alternatively the aqueous quench bottoms stream or degasified quench bottoms stream) is transported to a condensate stripper 58. The condensate stripper 58 is a distillation tower that fractionates the oxygenate hydrocarbons in the quench bottoms stream from water, catalyst and dissolved mineral salts in the quench bottoms stream. The fractionation results in a fractionation overhead stream and a fractionation bottoms stream.

Certain oxygenates are in the quench bottoms stream and are fed into the condensate stripper 58. Alcohols (e.g. methanol), aldehydes, ketones, that are in the quench bottoms stream are withdrawn through the fractionation overhead stream along line 62. The water, catalyst fines, organic acids and dissolved inorganic salts (including but not limited to inorganic salts of carbon dioxide) are withdrawn through the fractionation bottoms stream along line 60. The amount of oxygenates other than organic acids in the fractionation bottoms stream is less than 3,000 ppm preferably less than 2,000 ppm, more preferably less than 500 ppm based upon the composition of the fractionation bottoms stream.

The fractionation bottoms stream is transported along line 60 to wastewater treatment 64. In wastewater treatment, catalyst fines, if any, are separated from the wastewater and the water is further treated for release into the environment, as represented by line 66.

In one embodiment, the wastewater treatment 64 includes a settling device. A settling device is a device that separates solids from liquid by differences in their relative densities. A settling device includes but is not limited to settling ponds, settling tanks, clarifiers, centrifugal separators, and cyclonic separators are all examples of settling devices. The catalyst fines are separated from the first liquid portion forming concentrated catalyst fines and a clarified quench bottoms stream. The quench bottoms stream is clarified by the sedimentation of the catalyst fines in the settling device.

To aid in the efficient removal of catalyst fines from the fractionation bottoms stream (or alternatively the quench bottoms stream), a flocculent, optionally, is added. The flocculent enhances the settling of the catalyst fines to the bottom of the settling device. According to one embodiment, the time it takes for effective separation with the flocculent is about 2.5 hours or less, preferably about 2.0 hours or less, more preferably of about 1.5 hours or less, most preferably about 1.0 hours or less. In one embodiment the flocculent is a cationic polymer. Preferably, the flocculent is a cationic polymer selected from the group consisting of: polyacryamides, diallyldimethyl amonium chloride, epichlorohydrinamine, and dicandiamide-formaldehyde.

As previously described, the effluent stream is quenched to remove catalyst fines and water in the effluent stream and produces a quenched effluent stream. With continued reference to FIG. 2, the quenched effluent stream is withdrawn from the quench device 26 along line 30 to optional compressor 68. In one embodiment, the compressor is a single compression stage or comprises more than one compression stages. After compression, the quenched effluent stream travels along line 70 where, optionally, it is further processed by washing to remove carbon dioxide and other oxygenates and drying to remove water as described below.

Product Washing and Drying

Line 70 transports the quenched effluent stream to an optional oxygenate wash tower 72 which removes oxygenates by extraction with an oxygenate wash medium. An oxygenate wash medium is any medium that preferentially adsorbs oxygenates over olefin(s). The oxygenate wash tower 72 has an inlet stream comprising the oxygenate wash medium that enters the oxygenate wash tower 72 along line 74. The oxygenates are removed through the oxygenate wash tower bottoms along line 76 where it is transported and combined with the quench bottoms stream in line 56 or alternatively, lines 46 and/or 62.

All or a portion of the oxygenates such as ethers, aldehydes and/or ketones that are remaining in the quenched effluent stream are optionally removed during the oxygenate wash step. In one preferred embodiment, all or a portion of oxygenates such as dimethyl ether, acetaldehyde, acetone, propanal and/or propanone are optionally removed in the oxygenate wash tower 72.

In one embodiment of the invention, oxygenate wash medium is added to the oxygenate wash tower 72 in an amount sufficient to substantially reduce oxygenate content. It is preferred that oxygenate wash medium is added to the vessel at a molar ratio of oxygenate wash medium to quenched effluent stream from about 4:1 to about 1:5,000 based upon the total number of moles of the composition of the quenched effluent stream.

Higher molar ratios of oxygenate wash medium to quenched effluent stream are desirable for reducing oxygenate content; preferably from about 4:1 to about 1:1, more preferably from about 3:1 to about 1.2:1, and most preferably from about 2.5:1 to about 1.5:1.

Examples of oxygenate wash mediums include alcohols, amines, amides, nitriles, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

According to one embodiment, the wash is a two stage wash. The first stage wash uses a wash medium selected from any of wash medium embodiments described above, except water. The second stage wash medium is water.

The quenched effluent stream that passes through the oxygenate wash tower 72 is withdrawn along line 78 where it passes through an alkaline wash tower 80.

An alkaline wash medium is used to remove carbon dioxide from the quenched effluent stream by contacting quenched effluent stream with an alkaline wash medium according to one embodiment. The alkaline wash medium is an aqueous medium that has a pH greater than 7. Examples of such alkaline wash mediums include amines, potassium carbonate, and caustic. The term "caustic" as used herein refers to group 1 metal hydroxides such as potassium hydroxide and sodium hydroxide. Solutions containing amines and caustic compositions are preferred, with caustic compositions being more preferred.

Solutions containing aqueous amines, which are useful in an embodiment of this invention, contain any amine composition suitable as alkaline wash mediums. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations of any of the foregoing amine compositions can range from about 0.5 to about 8 moles of amine per liter of aqueous solution.

In one embodiment, piperazine and/or monomethylethanolamine (MMEA) is added to aqueous amine solutions to enhance their absorption capabilities. Preferably, these additives are included in the alkaline wash medium at a concentration of from about 0.04 to about 2 moles per liter of the alkaline wash medium in one embodiment of the invention.

The alkaline wash tower 80 of one embodiment has an alkaline wash stage 82 and a water wash stage 84. The quenched effluent stream, typically, enters at the bottom of the alkaline wash stage where it contacts an alkaline wash medium entering the alkaline wash stage along line 86. Preferably, alkaline wash medium removes any remaining carbon dioxide from the quenched effluent stream. In one embodiment, the alkaline wash stage has one or more discrete sections, optionally with or without separate pumparound streams, where caustic is introduced at different points at different concentrations. For example, the alkaline wash stage of one embodiment has a first section where alkaline wash medium is introduced at a concentration of 10 wt. %. The alkaline wash stage of the same embodiment has a second section where the alkaline wash medium is introduced at a concentration of 3 wt. %.

In an embodiment, the alkaline wash stage washes the quenched effluent stream with an alkaline stream having a pH greater than about 13. According to one embodiment, the alkaline stream, containing one or more alkaline compositions, has an alkaline concentration of 1 wt. % or more, preferably from about 1 wt. % to about 15 wt. %, more preferably from about 2 wt. % to about 5 wt. %, most preferably of about 3 wt. % based upon the total weight of the alkaline stream. In another embodiment the concentration of alkaline in the alkaline stream is from about 5 wt. % to about 20 wt. % preferably from about 5 wt. % to about 15 wt. % most preferably about 10 wt. % based upon the total weight of the alkaline stream. Any one or more of the alkaline compositions listed or represented above are added to the alkaline wash at the concentrations listed above. The alkaline content is adjusted to ensure essentially complete removal of carbon dioxide from the quenched effluent stream.

The used alkaline wash medium or alkaline stream is withdrawn along line 90. A portion of the used alkaline wash medium is pumped through pump 96 back to the alkaline wash stage. Fresh alkaline stream is combined with line 86 along line 88. Another portion of the used alkaline wash medium is transported along line 92 where it is added to the quench medium, typically in line 28, to adjust the pH thereof. Furthermore, a purge stream 93 is provided to purge carbon dioxide (in its acid salt form) as well as inorganic acids and other compounds that are alternatively and optionally removed from the quenched effluent stream in the alkaline wash tower. The quenched effluent stream passes through an additional stage of washing referred to as the water wash stage 84. Water is introduced into the top of the water wash stage 84 along line 98. The used water wash medium is withdrawn along line 100 where it is used or disposed of. The water wash removes any remaining alkaline wash medium in the quenched effluent stream or olefin stream. The water wash produces a washed effluent stream that is withdrawn along line 102 where it is dried and fractionated into specific product streams.

The washed effluent stream leaving the alkaline wash and water wash, of one embodiment, has a concentration of carbon dioxide of less than about 1000 ppb, preferably less than about 300 ppb, more preferably less than 50 ppb carbon dioxide based upon total weight of the washed effluent stream.

A drying step is optionally included. In this embodiment, a solid or liquid drying system can be used to remove water and/or additional oxygenate from the effluent stream.

In the solid drying system, the effluent stream having been quenched and optionally alkaline washed and water washed is contacted with a solid adsorbent to further remove water and oxygenates to very low levels. Typically, the adsorption process is carried out in one or more fixed beds containing a suitable solid adsorbent.

Adsorption is useful for removing water and oxygenates to very low concentrations, and for removing oxygenates that may not normally be removed by using other treatment systems. Preferably, an adsorbent system used as part of this invention has multiple adsorbent beds. Multiple beds allow for continuous separation without the need for shutting down the process to regenerate the solid adsorbent. By way of example and not by limitation, a three bed system typically has one bed that is on-line, one bed regenerated off-line, and a third bed on stand-by.

The specific adsorbent solid or solids used in the adsorbent beds depends on the types of contaminants being removed. Non-limiting examples of solid adsorbents for removing water and various polar organic compounds, such as oxygenates and absorbent liquids, include aluminas, silica, 3A molecular sieves, 4A molecular sieves, and alumino-silicates. Beds containing mixtures of these sieves or multiple beds having different adsorbent solids are used to remove water, as well as a variety of oxygenates in one embodiment.

In an embodiment of the present invention, one or more adsorption beds are arranged in series or parallel. In one example of a series arrangement, a first bed is used to remove the smallest and most polar molecules, which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13× and/or a high surface area active alumina.

In another embodiment, the first bed is a 3.6 A molecular sieve capable of selectively separating both water and methanol from the hydrocarbons in the olefin stream. This first bed can then be followed by one or more 13× or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the effluent stream. The water absorbent can be any liquid effective in separating water from an olefin stream. Preferably, the water absorbent is a polyol or an alcohol, such as ethanol or methanol.

The step of drying produces a dried effluent stream that is hereinafter referred to as the olefin product stream.

Preferably, the olefin product stream contains less than about 100 wppm water, more preferably less than about 10 wppm, and most preferably less than 1 wppm based upon the weight of the olefin product stream. Preferably less than about 10 wppm, more preferably less than about 5 wppm, and most preferably less than about 1 wppm dimethyl ether is present in the dried olefin stream.

Product Recovery

The dried olefin stream, or olefin product stream, is further processed to isolate and purify components in the olefin product stream, particularly, ethylene and propylene. There are many well-known recovery systems, techniques and sequences that are useful in separating olefin(s) and purifying olefin(s) in the olefin product stream. Recovery systems generally comprise one or more or a combination of a various separation, fractionation and/or distillation towers, columns, splitters, or trains, reaction systems and other associated equipment, for example, various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a dethanizer, a depropanizer, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefin(s) without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefin(s), such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in an oxygenate-to-olefin process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example, for the purification of olefin(s), are described in Kirk-Othmer Encyclopedia of Chemical Technology, 4th Edition, Volume 9, John Wiley & Sons, 1996, pages 249–271 and 894–899, which is herein incorporated by reference. Purification systems are also described in, for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the olefin product stream withdrawn from the reactor or converting those products produced as a result of the recovery system utilized.

In one embodiment, the olefin product stream is passed through a recovery system producing one or more hydrocarbon containing stream(s), in particular, a three or more carbon atom (C3+) hydrocarbon containing stream. In this embodiment, the C3+hydrocarbon containing stream is passed through a first fractionation zone producing a crude C3 hydrocarbon and a C4+hydrocarbon containing stream, the C4+hydrocarbon containing stream is passed through a second fractionation zone producing a crude C4 hydrocarbon and a C5+hydrocarbon containing stream. The four or more carbon hydrocarbons include butenes such as butene-1 and butene-2, butadienes, saturated butanes, and isobutanes.

The olefin product stream removed from a conversion process, particularly an oxygenate-to-olefin process, typically contains hydrocarbons having 4 or more carbon atoms. The amount of hydrocarbons having 4 or more carbon atoms is typically in an amount less than 30 weight percent, preferably less than 25 weight percent, more preferably less than 20 weight percent, and most preferably less than 15 weight percent, based on the total weight of the olefin product stream withdrawn from an oxygenate-to-olefin process, excluding water. In particular with a conversion process of oxygenates into olefin(s) utilizing a molecular sieve catalyst composition the resulting olefin product stream typically comprises a majority of ethylene and/or propylene and a lesser amount of four carbon and higher carbon number products and other by-products, excluding water.

The preferred light olefin(s) produced by any one of the processes described above, preferably conversion processes, are high purity prime olefin(s) products that contains a CX olefin, wherein x is a number from 2 to 4, in an amount greater than 80 wt. %, preferably greater than 90 wt. %, more preferably greater than 95 wt. %, and most preferably no less than about 99 wt. %, based on the total weight of the olefin. The purity of the olefin(s) is preferably of a grade that makes the use of the olefin(s) acceptable for one or more applications discussed below.

Olefin Product Use

Suitable well-known reaction systems that follow the recovery system primarily take lower value products and convert them to higher value products. For example, the C4 hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems that take lower value products and convert them to higher value products include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287,369 and 5,763,678 (carbonylation or hydroformulation of higher olefin(s) with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., Process for Upgrading C3, C4 and C5 Olefinic Streams, Pet. & Coal, Vol. 37, No. 4 (1995) (dimerizing or oligomerizing propylene, butylene and pentylene), which are all herein fully incorporated by reference.

Other uses for one or more olefin product(s) are disclosed in U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in the olefin product stream fed to another reactor) PCT WO 01/60770 published Aug. 23, 2001 and U.S. patent application Ser. No. 09/627, 634 filed Jul. 28, 2000 (high pressure), U.S. patent application Ser. No. 09/507,838 filed Feb. 22, 2000 (staged feedstock injection), and U.S. patent application Ser. No. 09/785, 409 filed Feb. 16, 2001 (acetone co-fed), which are all herein fully incorporated by reference.

In another embodiment, olefin(s) produced are directed to, in one embodiment, one or more polymerization processes for producing various polyolefin(s). (See for example, U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352,749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281, 300 describe slurry phase polymerization processes; U.S. Pat. Nos. 4,271,060, 5,001,205, 5,236,998 and 5,589,555 describe solution phase polymerization processes; and U.S. Pat. Nos. 3,917,577, 4,175,169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076,698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the present invention comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefin(s)(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kpag), preferably in the range of from about 200 psig (1379 kPag) to about 500 psig (3448 kPag), and more preferably in the range of from about 250 psig (1724 kpag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight (Mw/Mn) of greater than 1.5 to about 10 as measured by gel permeation chromatography, a melt index (I2) as measured by ASTM-D-1238-E in the range from 0.01 dg/min to 1000 dg/min, a melt index ratio (I21/I2) (I21 is measured by ASTM-D-1238-F) of from 10 to less than 25, alternatively a I21/I2 of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, vessels, large hollow articles, rigid food containers and toys, etc.

In addition to polyolefin(s), numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefin(s), vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

The foregoing description of the invention including but not limited to drawings and examples are intended to illustrate one or more embodiments of the invention and are non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention.

What is claimed is:

1. A process for producing olefin(s) from oxygenate(s), the process comprising the steps of:
    (a) contacting an oxygenate feed stream with an oxygenate-to-olefin catalyst to produce an effluent stream by using a quench medium comprising carbon dioxide, oxygenate(s), water and olefin(s);
    (b) quenching the effluent stream to produce a quench bottoms stream comprising carbon dioxide, oxygenate(s) and water and a quenched effluent stream comprising olefins(s) wherein the quench medium has a pH ranging from about 7.1 to about 11.5;
    (c) separating carbon dioxide from the quench bottoms stream wherein the separating further comprises combining an acidic composition with the quench bottoms stream;
    (d) separating a majority of the oxygenate(s) from a majority of the water in the quench bottoms stream; and
    (e) combining the majority of the oxygenate(s) with the oxygenate feed stream.

2. The process of claim 1, wherein the acidic composition comprises an inorganic acid.

3. The process of claim 2, wherein the inorganic acid comprises an inorganic acid selected from the group consisting of hydrochloric acid, nitric acid, sulfuric acid and mixtures thereof.

4. The process of claim 1, wherein the acidic composition comprises an organic acid.

5. The process of claim 4, wherein the organic acid comprises acetic acid.

6. The process of claim 1 further comprising separating the quench bottoms stream into a hydrocarbon phase and an aqueous phase.

7. The process of claim 6, wherein the hydrocarbon phase comprises aromatic hydrocarbons.

8. The process of claim 6, wherein the hydrocarbon phase comprises products of aldol condensation of aldehydes and/or ketones.

9. The process of claim 6, wherein the aqueous phase comprises organic acids.

10. The process of claim 6, wherein the aqueous phase comprises alcohol.

11. The process of claim 6, wherein the aqueous phase comprises catalyst fines.

12. The process of claim 1, wherein the step of (c) separating removes more than 10 wt. % of the carbon dioxide in the quench bottoms stream.

13. The process of claim 1, wherein the quench medium comprises the aqueous phase of the quench bottoms stream.

14. The process of claim 1, wherein the step of (c) separating occurs at a pH ranging from about 6 to about 9.

* * * * *